(12) United States Patent  (10) Patent No.: US 8,568,463 B2
Hamada et al.  (45) Date of Patent: Oct. 29, 2013

(54) HAIR GROWTH MODULATING METHOD AND MODULATION DEVICE THEREOF

(75) Inventors: Chosei Hamada, Kadoma (JP); Masato Kinoshita, Kadoma (JP); Kaori Naganuma, Kadoma (JP); Takashi Matsuzaki, Matsue (JP)

(73) Assignees: Panasonic Corporation, Osaka (JP); National University Corporation Shimane University, Shimane (JP)

( * ) Notice: Subject to any disclaimer, the term of this patent is extended or adjusted under 35 U.S.C. 154(b) by 743 days.

(21) Appl. No.: 12/593,577

(22) PCT Filed: Dec. 25, 2007

(86) PCT No.: PCT/JP2007/074862
§ 371 (c)(1),
(2), (4) Date: Sep. 28, 2009

(87) PCT Pub. No.: WO2008/129741
PCT Pub. Date: Oct. 30, 2008

(65) Prior Publication Data
US 2010/0121417 A1    May 13, 2010

(30) Foreign Application Priority Data
Mar. 30, 2007  (JP) ................................ 2007-094805

(51) Int. Cl.
*A61N 5/06*  (2006.01)
(52) U.S. Cl.
USPC .................. 607/88; 607/89; 607/90; 607/91; 607/92; 607/93; 606/9; 128/898

(58) Field of Classification Search
USPC ................... 607/88–93; 606/9; 128/896, 898
See application file for complete search history.

(56) References Cited

U.S. PATENT DOCUMENTS

| 5,860,967 A * | 1/1999 | Zavislan et al. ................... 606/9 |
| 8,388,669 B2 * | 3/2013 | Hamada et al. ................. 607/88 |
| 2004/0015214 A1 * | 1/2004 | Simkin et al. ................... 607/88 |
| 2004/0162596 A1 * | 8/2004 | Altshuler et al. ............... 607/88 |
| 2006/0063990 A1 | 3/2006 | Cho et al. |
| 2006/0161226 A1 * | 7/2006 | McMickle ...................... 607/88 |

(Continued)

FOREIGN PATENT DOCUMENTS

| CN | 1739449 A | 3/2006 |
| JP | 2003-12487 A | 1/2003 |

(Continued)

OTHER PUBLICATIONS

Notification of Reasons for Refusal for the Application No. 2007-094805 from Japan Patent Office mailed Feb. 7, 2012.

(Continued)

*Primary Examiner* — Jessica Stultz
*Assistant Examiner* — Delma R Forde
(74) *Attorney, Agent, or Firm* — McDermott Will & Emery LLP

(57) ABSTRACT

A modulating light having a wavelength of 600 nm to 1000 nm excluding a range of 870 nm to 910 nm is irradiated to a portion around hair roots such that a light absorptive component existing in a human body around the hair roots absorbs the light for modulating hair growth. The light having the wavelength in the above range enhances hair growth free from causing inflammation, yet safely and gentle to skin.

8 Claims, 11 Drawing Sheets

(56) References Cited

U.S. PATENT DOCUMENTS

| | | | |
|---|---|---|---|
| 2007/0179573 A1* | 8/2007 | Laurent | 607/89 |
| 2008/0125835 A1* | 5/2008 | Laurent | 607/89 |
| 2008/0287931 A1* | 11/2008 | Jones et al. | 606/9 |
| 2009/0270845 A1* | 10/2009 | Birmingham et al. | 606/2 |
| 2011/0015707 A1* | 1/2011 | Tucker et al. | 607/90 |
| 2011/0238138 A1* | 9/2011 | Takada | 607/88 |
| 2012/0016174 A1* | 1/2012 | De Taboada et al. | 600/2 |
| 2012/0130455 A1* | 5/2012 | Baird et al. | 607/90 |

FOREIGN PATENT DOCUMENTS

| | | |
|---|---|---|
| JP | 2005-512620 A | 5/2005 |
| JP | 2006-501960 A | 1/2006 |
| RU | 2 045 972 C1 | 10/1995 |
| WO | WO-99/07438 A1 | 2/1999 |
| WO | WO-03/039478 A2 | 5/2003 |
| WO | WO-2004/033040 A1 | 4/2004 |

OTHER PUBLICATIONS

Russian Official Action for the Application No. 2009140046 dated Nov. 22, 2010.

International Search Report for the Application No. PCT/JP2007/074862 mailed Jan. 29, 2008.

Chung, Phil S., et al., "The Effect of Low-Power Laser on the Murine Hair Growth", Journal of the Korean Society Plastic & Reconstructive Surgeons, 2004, pp. 1-8.

Taiwanese Office Action for the Application No. 096150003 from Taiwan Patent Office dated Oct. 13. 2010.

Chinese Office Action, and English translation thereof, issued in Chinese Patent Application No. 200780052445.2 mailed Jun. 29, 2012.

\* cited by examiner (A)

(B)

850nm 50mW/cm²

HAIR GROWTH MODULATING METHOD AND MODULATION DEVICE THEREOF

TECHNICAL FIELD

The present invention relates to a hair growth modulating method that is used when modulating hair growth using light, and a modulation device thereof.

BACKGROUND ART

A method for regenerating hair is known in which hair growth is accelerated by causing a mild inflammation in the skin. Although highly effective methods consist of causing an inflammation with drugs and the like, the use of such drugs frequently causes mild chapped skin as well as problems such as pain or infection.

In addition, although the Journal of the Korean Society Plastic & Reconstructive Surgeons, 2004, p. 1-p. 8 advocates the regeneration of hair by irradiating light having a wavelength of 890 nm, when the effects of using light having a wavelength of 890 nm were confirmed in animal experiments, this technique was determined to utilize the occurrence of inflammation within the skin in the same manner as in the case of using drugs as mentioned above, and the artificial induction of such inflammation is undesirable for the human body.

DISCLOSURE OF THE INVENTION

With the foregoing in view, an object of the present invention is to provide a hair growth modulating method capable of promoting hair growth without causing inflammation, and a modulation device thereof.

The hair growth modulating method as claimed in the present invention is characterized in that hair growth is modulated by irradiating modulating light having a wavelength of 600 nm to 1000 nm excluding a range of 870 nm to 910 nm, to a portion around hair roots of a human body such that the modulating light is absorbed by a light absorptive component of the human body existing around the hair roots. The use of modulating light of this wavelength range enables hair growth effects to be obtained without causing inflammation, thereby enabling hair growth to be promoted in a manner that is safe and gentle to the skin.

The energy imparted by the modulating light is preferably 10 $J/cm^2$ to 100 $J/cm^2$.

The irradiation time of the modulating light is 1 minute to 30 minutes per day for 3 to 10 consecutive days.

The modulating light may be flashed at a frequency of 100 Hz to 1000 Hz.

The present invention also proposes a device that realizes the hair growth modulating method described above, and is provided with a light irradiator configured to irradiate the above-mentioned modulating light.

BEST MODE FOR CARRYING OUT THE INVENTION

Figure 1:
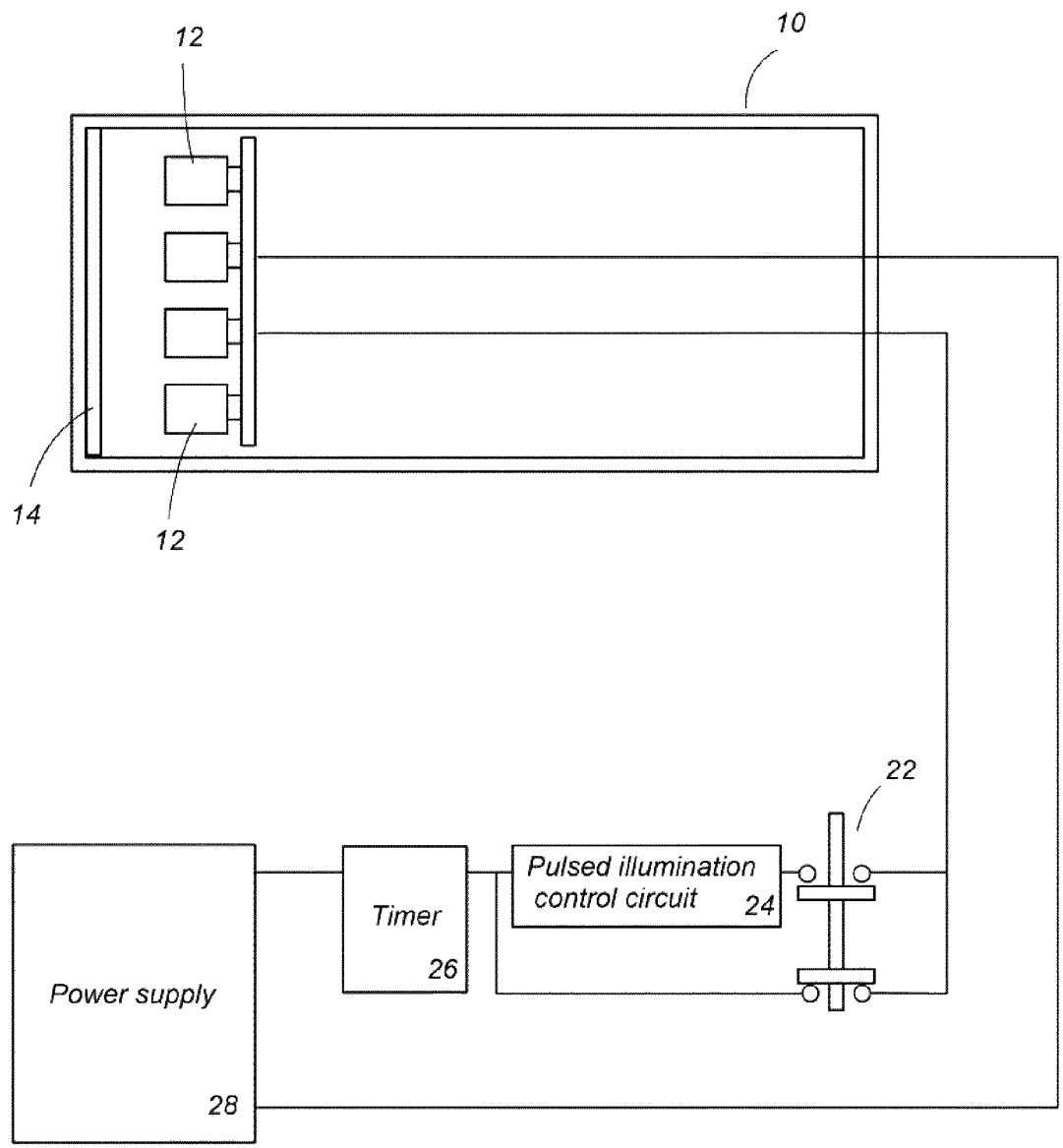
FIG. 1 is a block diagram of a hair growth modulation device in the present invention.

The following provides an explanation of the present invention based on embodiments shown in the attached drawings. FIG. 1 shows a hair growth modulation device in the present invention. This hair growth modulation device comprises a housing having a cylindrical shape to have its diameter of about 20 mm, and a plurality of light emitting diodes which are arranged within the housing 10. A plurality of the light emitting diodes 12 are configured to irradiate the skin with the modulating light through a glass plate 14 on the front end of the housing 10.

Light emitting diodes that output light of a wavelength of 950 nm are used for the light emitting diodes 12, and are connected to a selector switch 22, a pulsed illumination control circuit 24, and a power supply 28 through a timer 26. The selector switch 22 is configured so as to enable selection of pulsed illumination of the light emitting diodes 12 at 500 Hz or continuous illumination of the light emitting diodes 12 under the control of the pulsed illumination control circuit 24, while the timer 26 limited irradiation time to a prescribed time such as 20 minutes.

The irradiation power of modulating light irradiated from the light emitting diodes 12 is 50 $mW/cm^2$ during continuous illumination, and is 100 $mW/cm^2$ in the case of pulsed illumination at 500 Hz, which is higher than in the case of continuous illumination. Irradiation energy ($J/cm^2$) is the product of irradiation power (W) and irradiation time (seconds), and irradiation power P (W) and irradiation time S (seconds) are controlled so that the irradiation energy is 10 $J/cm^2$ to 100 $J/cm^2$. If the irradiation energy is less than 10 $J/cm^2$, the irradiation time becomes excessively long, while if the irradiation energy exceeds 100 $J/cm^2$, heat becomes excessive.

Figure 2:
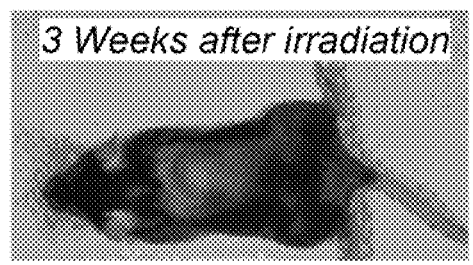
FIGS. 2(A) and 2(B) are explanatory drawings showing hair growth effects in the case of using modulating light of a wavelength of 950 nm.
Figure 2:
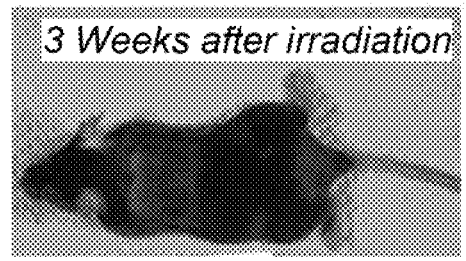

Although hair (body hair and scalp hair) is known to have a hair cycle in which hair changes from a growth period to a regressive period and then to a rest period, the results conducting an experiment involving irradiating modulating light in mouse in which hair growth was in the rest period are shown in FIGS. 2(A) and 2(B). Furthermore, hair growth in mice in this state normally does not begin for about 8 weeks.

FIG. 2(A) shows a mouse in which 3 weeks have passed since irradiating with continuously illuminated modulating light for 20 minutes per day for 5 consecutive days, while FIG. 2(B) shows a mouse in which 3 weeks have passed since irradiating with pulsed illuminated modulating light for 20 minutes per day for 5 consecutive days. Hair growth was observed over half the backs of the animals in both cases.

Figure 3:
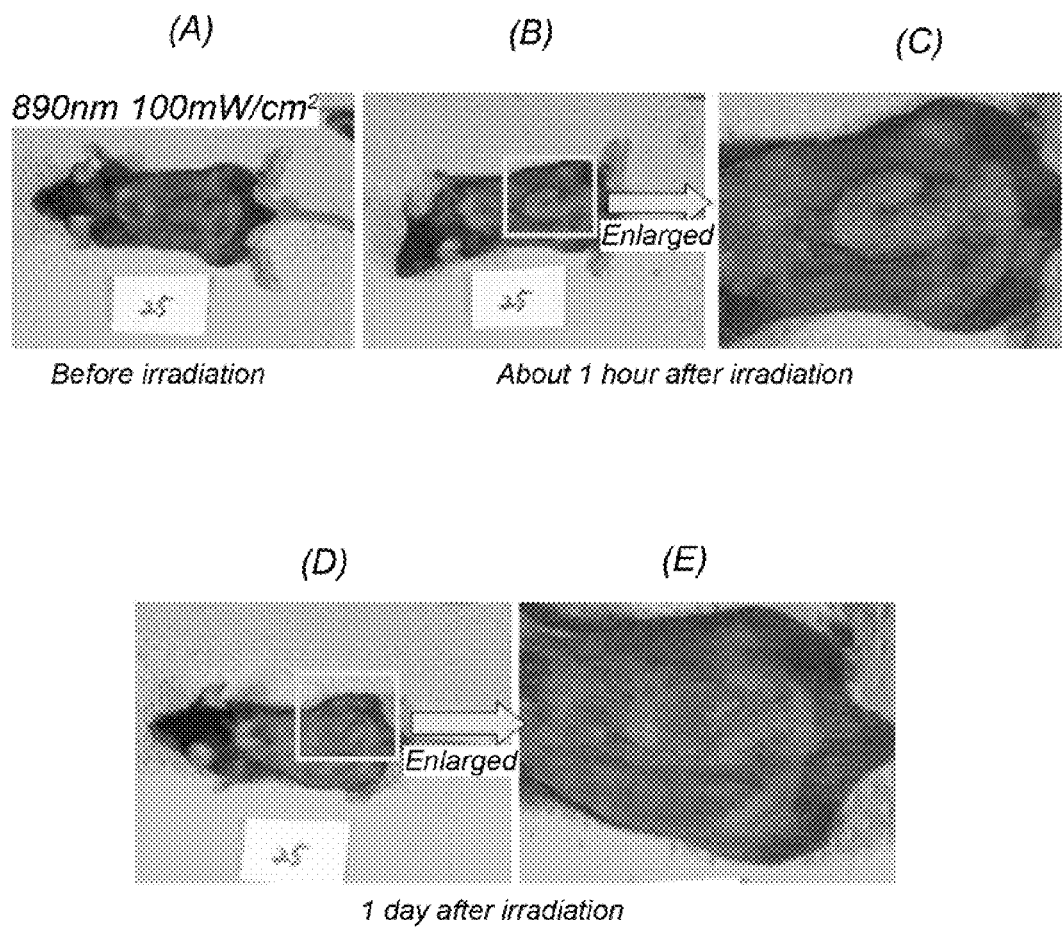
FIGS. 3(A) to 3(E) are explanatory drawings showing hair growth effects and the occurrence of inflammation in the case of using modulating light of a wavelength of 890 nm.

In contrast, the case of irradiating with light of a wavelength of 890 nm as indicated in the examples of the prior art (using a light emitting diode for the light source) in the form of pulsed illumination at 500 Hz and at an irradiation power of 100 mW/cm$^2$ is shown in FIGS. 3(A) to 3(E). FIG. 3(A) shows a mouse prior to irradiation, FIGS. 3(B) and 3(C) show a mouse 1 hour after irradiation, and FIGS. 3(D) and 3(E) show a mouse 1 day after irradiation. Obvious inflammation (blisters) occurred within the skin, and this inflammation reached the skin surface after several days. Since this inflammation does not occur during irradiation with light of a wavelength of 950 nm, it was clear that the occurrence of adverse effects is low in the case of using light of a wavelength of 950 nm.

Figure 4:
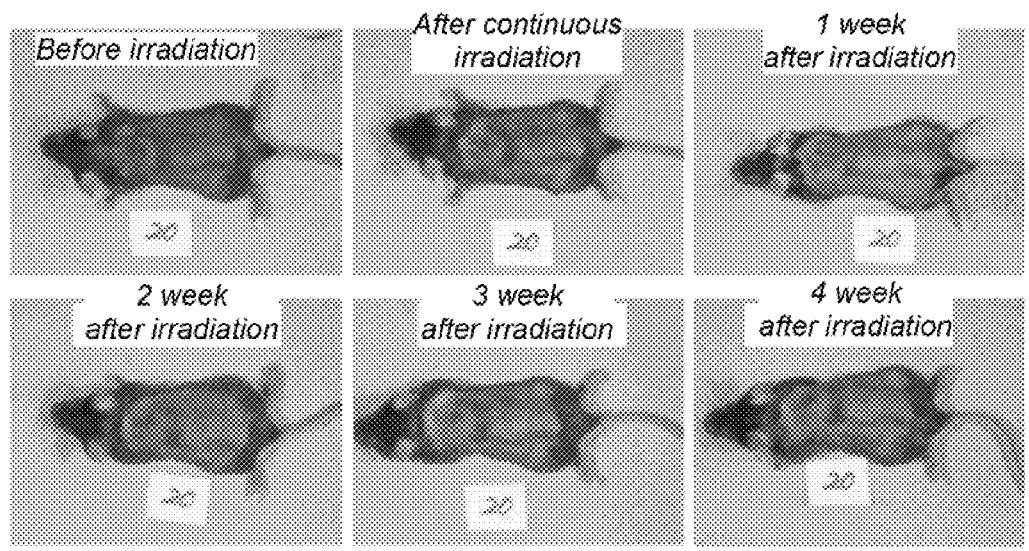
FIG. 4 is an explanatory drawing showing hair growth effects resulting from the use of modulating light of a wavelength of 626 nm and at an irradiation power of 50 $mW/cm^2$.
Figure 5:
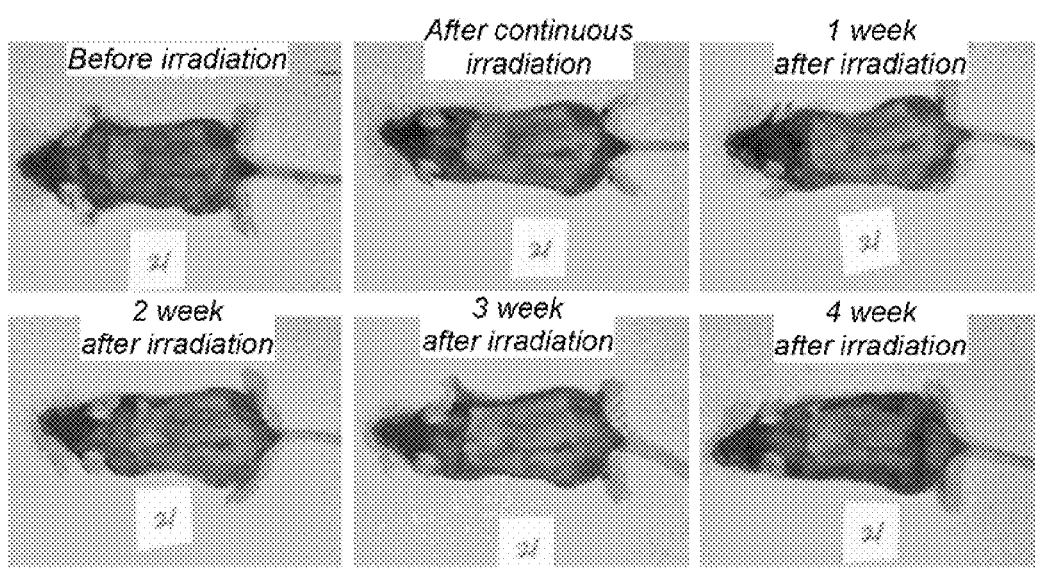
FIG. 5 is an explanatory drawing showing hair growth effects resulting from the use of modulating light of a wavelength of 626 nm and at an irradiation power of 100 $mW/cm^2$.

FIGS. 4 and 5 show each of the resulting states for before irradiation, after continuous irradiation, 1 week after irradiation, 2 weeks after irradiation, 3 weeks after irradiation and 4 weeks after irradiation for the case of irradiating with modulating light of a wavelength of 626 nm at an irradiation power of 50 mW/cm$^2$ for 20 minutes per day for 5 consecutive days using continuous illumination, and the case of irradiating with the same modulating light at an irradiation power of 100 mW/cm$^2$ for 20 minutes per day for 5 consecutive days using pulsed illumination.

Figure 6:
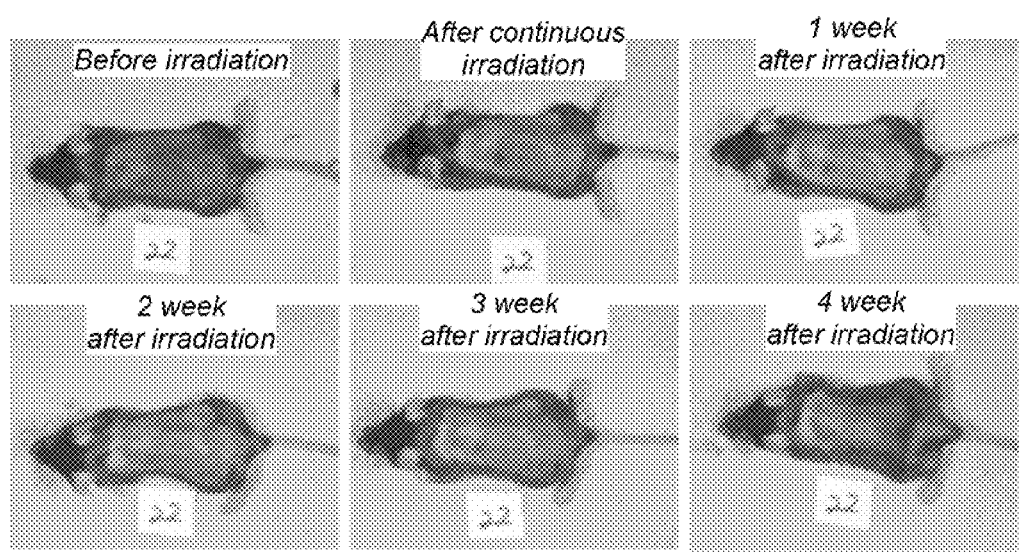
FIG. 6 is an explanatory drawing showing hair growth effects resulting from the use of modulating light of a wavelength of 850 nm and at an irradiation power of 50 $mW/cm^2$.
Figure 7:
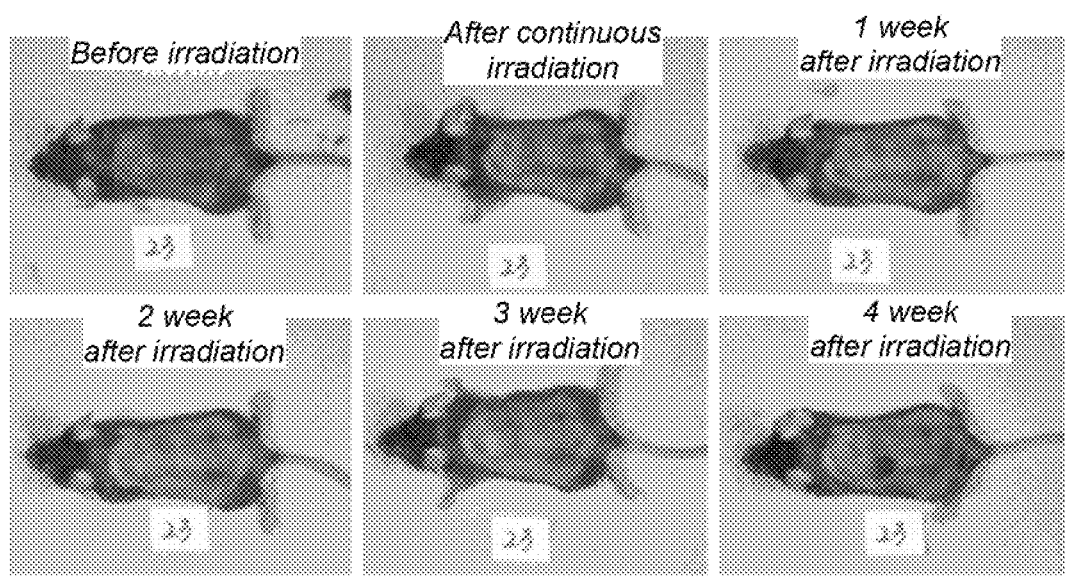
FIG. 7 is an explanatory drawing showing hair growth effects resulting from the use of modulating light of a wavelength of 850 nm and at an irradiation power of 100 $mW/cm^2$.

FIGS. 6 and 7 show each of the resulting states for the case of irradiating with modulating light of a wavelength of 850 nm at an irradiation power of 50 mW/cm$^2$ for 20 minutes per day for 5 consecutive days using continuous illumination, and the case of irradiating with the same modulating light at an irradiation power of 100 mW/cm$^2$ for 20 minutes per day for 5 consecutive days using pulsed illumination.

Figure 8:
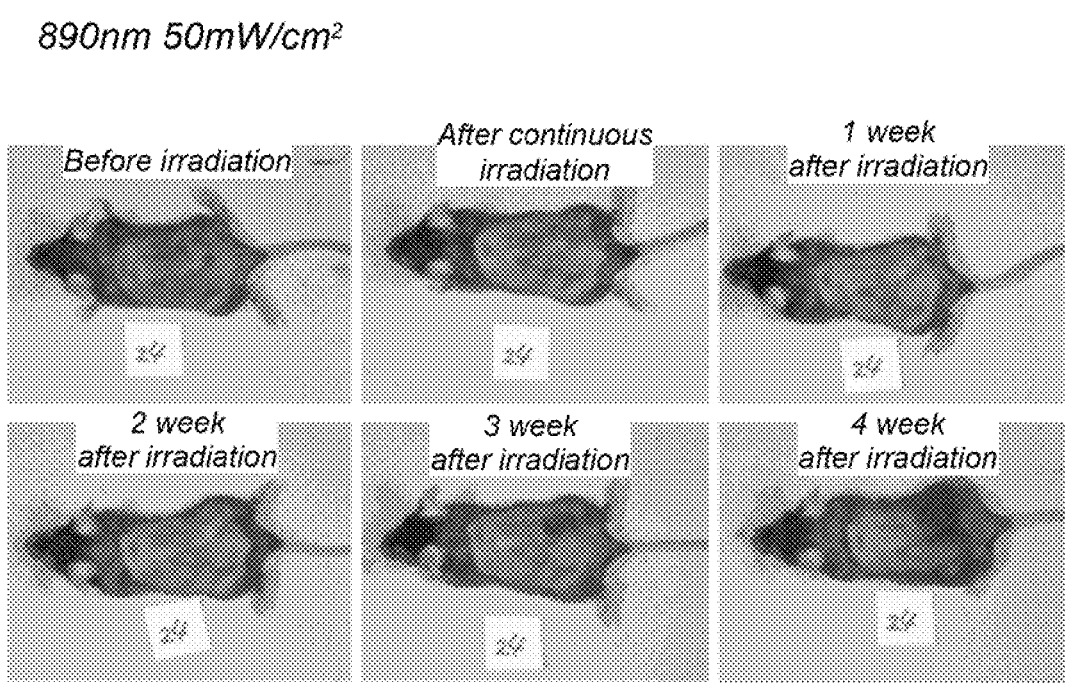
FIG. 8 is an explanatory drawing showing hair growth effects resulting from the use of modulating light of a wavelength of 890 nm and at an irradiation power of 50 $mW/cm^2$.
Figure 9:
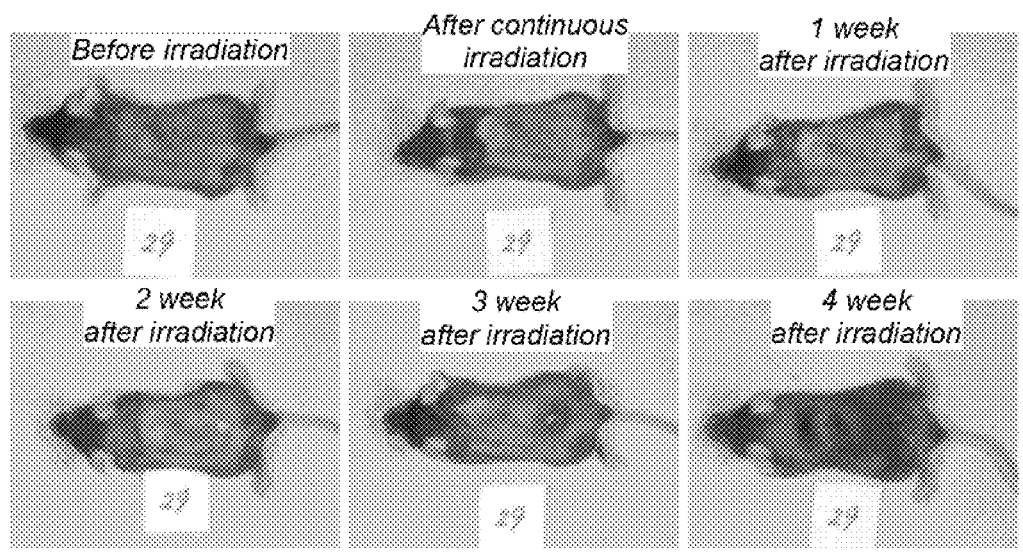
FIG. 9 is an explanatory drawing showing hair growth effects resulting from the use of modulating light of a wavelength of 890 nm and at an irradiation power of 100 $mW/cm^2$.

FIGS. 8 and 9 show each of the resulting states for before irradiation, after continuous irradiation, 1 week after irradiation, 2 weeks after irradiation, 3 weeks after irradiation and 4 weeks after irradiation for the case of irradiating with modulating light of a wavelength of 890 nm at an irradiation power of 50 mW/cm$^2$ for 20 minutes per day for 5 consecutive days using continuous illumination, and the case of irradiating with the same modulating light at an irradiation power of 100 mW/cm$^2$ for 20 minutes per day for 5 consecutive days using pulsed illumination.

Figure 10:
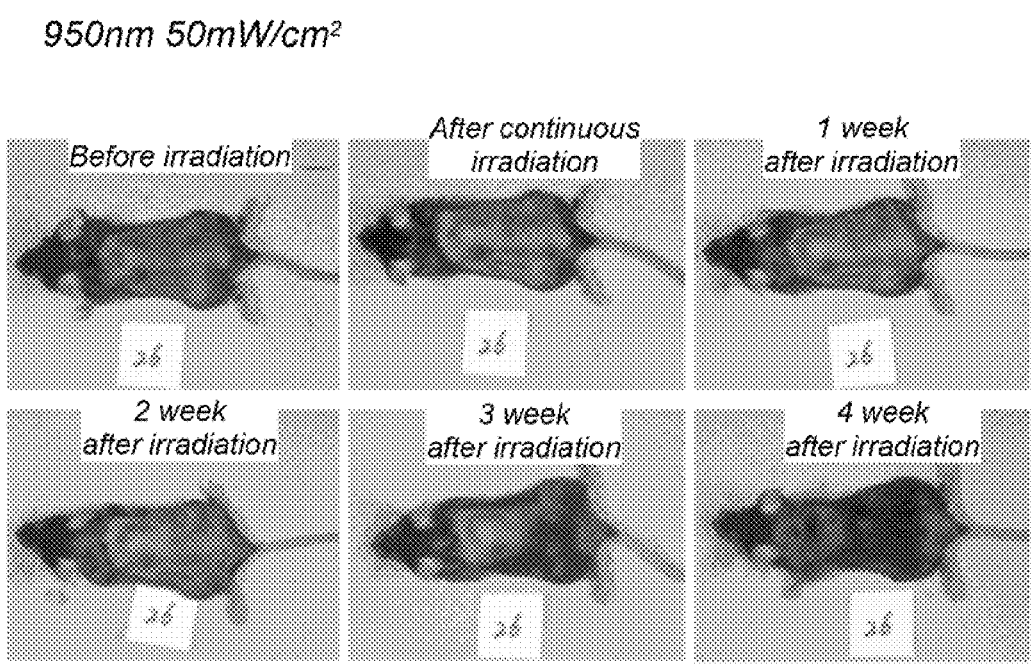
FIG. 10 is an explanatory drawing showing hair growth effects resulting from the use of modulating light of a wavelength of 950 nm and at an irradiation power of 50 $mW/cm^2$.
Figure 11:
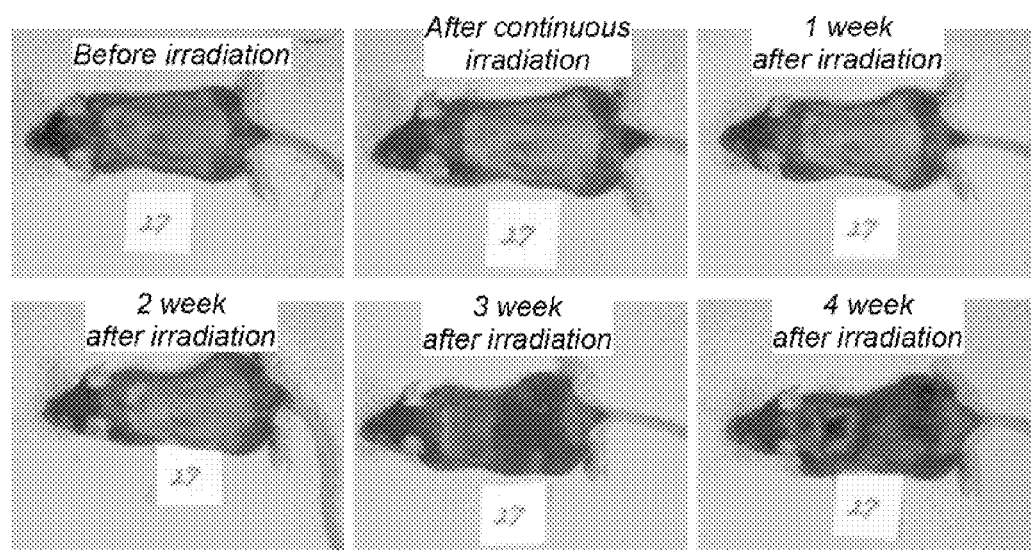
FIG. 11 is an explanatory drawing showing hair growth effects resulting from the use of modulating light of a wavelength of 950 nm and at an irradiation power of 100 $mW/cm^2$.

FIGS. 10 and 11 show each of the resulting states for the case of irradiating with modulating light of a wavelength of 950 nm at an irradiation power of 50 mW/cm$^2$ for 20 minutes per day for 5 consecutive days using continuous illumination, and the case of irradiating with the same modulating light at an irradiation power of 100 mW/cm$^2$ for 20 minutes per day for 5 consecutive days using pulsed illumination.

In all cases, hair growth effect was confirmed in the fourth week after irradiation. However, the irradiation of the light having the wavelength of 890 nm caused inflammation of the skin. In contrast, the irradiation of the light having the wavelengths of 950 nm, 626 nm and 850 nm did not cause the inflammation of the skin.

Furthermore, since light of a wavelength of less than 600 nm is absorbed by melanin in the body, the above-mentioned hair growth effects cannot be expected to be demonstrated to a great extent, while light of a wavelength of greater than 1000 nm has the risk of causing harmful events since this is the absorption wavelength of water in the body.

In addition, when the irradiation energy of modulating light is less than 10 J/cm$^2$, hair growth effects also cannot be expected to be demonstrated to a great extent, while when the irradiation energy of modulating light exceeds 100 J/cm$^2$, thermal irritation of the body increases resulting in problems.

Setting the irradiation time of the modulating light to 1 minute to 30 minutes per day and irradiating for 3 to 10 consecutive days was effective. Although only surmised, this is thought to be related to it being about 24 hours after irradiation of light until mRNA is formed in the body that leads to the formation of protein for promoting a reaction after which changes begin.

Moreover, results were obtained indicating that flashing modulating light at a frequency of 100 Hz to 1000 Hz is more preferable than continuous illumination. Although the biological reason why pulsed illumination is more effective is unclear, it is thought that the proportion of light energy that changes to thermal energy is higher in the case of continuous illumination than in the case of pulsed illumination.

The invention claimed is:

1. A hair growth promoting method comprising a step of irradiating a modulating light, which includes a wavelength of 950 nm and excluding a range of 870 nm to 910 nm, to a portion around hair roots of a human body such that the modulating light is absorbed by a light absorptive component of the human body existing around the hair roots for promoting the hair growth.

2. The hair growth promoting method as set forth in claim 1, wherein said modulating light has an energy of 10 J/cm$^2$ to 100 J/cm$^2$.

3. The hair growth promoting method as set forth in claim 2, wherein said modulating light is irradiated for a period of 1 minute to 30 minutes per day over 3 to 10 consecutive days.

4. The hair growth promoting method as set forth in claim 3, wherein said modulating light is flashed at a frequency of 100 Hz to 1000 Hz.

5. The hair growth promoting method as set forth in claim 2, wherein said modulating light is flashed at a frequency of 100 Hz to 1000 Hz.

6. The hair growth promoting method as set forth in claim 1, wherein said modulating light is irradiated for a period of 1 minute to 30 minutes per day over 3 to 10 consecutive days.

7. The hair growth promoting method as set forth in claim 6, wherein said modulating light is flashed at a frequency of 100 Hz to 1000 Hz.

8. The hair growth promoting method as set forth in claim 1, wherein said modulating light is flashed at a frequency of 100 Hz to 1000 Hz.

* * * * *